United States Patent [19]

Benoit et al.

[11] Patent Number: 5,336,670
[45] Date of Patent: Aug. 9, 1994

[54] 2,2-DIMETHYL-3-(BUT-1-EN-3-YNYL)-CYCLOPROPANE CARBOXYLATES

[75] Inventors: Marc Benoit, Roouevaire; Jean-Pierre Demoute, Neuilly Plaisance; Jean-Marc Girodeau, Chelles, all of France

[73] Assignee: Roussel-Uclaf, France

[21] Appl. No.: 992,452

[22] Filed: Dec. 17, 1992

[30] Foreign Application Priority Data

Feb. 21, 1992 [FR] France ................ 92 02009

[51] Int. Cl.$^5$ .................... A01N 55/00; C07C 69/743
[52] U.S. Cl. ...................... 514/63; 514/521; 514/531; 556/416; 556/437; 556/438; 558/407; 558/434; 560/124
[58] Field of Search ................ 558/407, 434; 514/521, 514/531, 63; 556/416, 437, 438; 560/124

[56] References Cited

U.S. PATENT DOCUMENTS 5,135,951  8/1992  Babin et al. .................... 558/407 X
5,192,801  3/1993  Babin et al. .................... 558/407 X

FOREIGN PATENT DOCUMENTS 0031041  7/1981  European Pat. Off. .
0381563  8/1990  European Pat. Off. .
0378026  7/1990  France .

OTHER PUBLICATIONS

The Journal of Organic Chemistry Jul. 7, 1991, vol. 56: No. 12; minato.

Primary Examiner—Joseph Paul Brust
Attorney, Agent, or Firm—Bierman and Muserlian

[57] ABSTRACT

Compounds of the formula

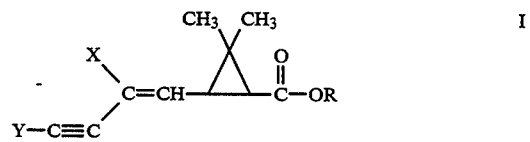

wherein X is hydrogen, halogen or an optionally substituted alkyl, Y is selected from the group consisting of hydrogen, halogen optionally substituted alkyl, an optionally substituted aryl or arylalkyl, —(CH$_2$)$_m$ Si (Alk$_1$)$_3$, —(CH$_2$)$_n$ OAlk$_2$ or —(CH$_2$)$_p$ SAlk$_3$, m, n and p are an integer from 0 to 6, Alk$_1$, Alk$_2$ and Alk$_3$ are alkyl and R is alkyl of 1 to 18 carbon atoms or the remainder of an alcohol used in the pyrethrinoid series having pesticide properties.

12 Claims, No Drawings

2,2-DIMETHYL-3-(BUT-1-EN-3-YNYL)-CYCLOPROPANE CARBOXYLATES

OBJECTS OF THE INVENTION

It is an object of the invention to provide the novel compounds of Formula I and a process and intermediates for their preparation.

It is another object of the invention to provide novel pesticidal compositions and to provide a novel method of combatting pests.

These and other objects and advantages of the invention will become obvious from the following detailed description.

THE INVENTION

The novel compounds of the invention have the formula

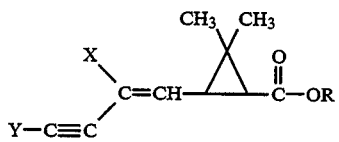

in all its possible stereoisomer forms and mixtures thereof wherein X is selected from the group consisting of hydrogen, halogen and alkyl, alkenyl, alkynyl and cycloalkyl of up to 8 carbon atoms optionally substituted by at least one halogen, Y is selected from the group consisting of a) alkyl, alkenyl, alkynyl and cycloalkyl of up to 8 carbon atoms optionally substituted with at least one member of the group consisting of halogen, —CN, —OH and alkoxy of 1 to 7 carbon atoms, b) aryl and aralkyl of up to 16 carbon atoms optionally substituted with at least one member of the group consisting of halogen, alkyl and alkoxy of 1 to 8 carbon atoms, —$(CH_2)_m$—$SiAlk_1)_3$, —$(CH_2)_n$—$OAlk_2$, —$(CH_2)_p$—$SAlk_3$, halogen and hydrogen, m, n and p are integers from 0 to 6, $Alk_1$, $Alk_2$ and $Alk_3$ being alkyl or cycloalkyl of up to 8 carbon atoms and R is alkyl of up to 18 carbon atoms or the residue of a pyrethrinoid alcohol.

When X or Y is halogen, it is preferably fluorine, chlorine or bromine and when X or Y is alkyl or cycloalkyl, it is preferably methyl, ethyl, n-propyl, isopropyl, n-butyl, isobutyl, tert-butyl, pentyl, hexyl, vinyl, 1,1-dimethyl-allyl, ethynyl, propynyl, cyclopropyl, cyclobutyl, cyclopentyl or cyclohexyl, all optionally substituted by at least one fluorine, chlorine or bromine with X preferably being $CF_3$.

Aryl is preferably phenyl and aralkyl preferably is benzyl or phenethyl. $Alk_1$, $Alk_2$ and $Alk_3$ preferably are methyl, ethyl or propyl.

When Y is aryl or aralkyl substituted by at least one alkyl or alkoxy, the alkyl or alkoxy is preferably methyl, ethyl, isopropyl, n-propyl, n-butyl, isobutyl or tert-butyl, methoxy, ethoxy, n-propoxy, isopropoxy, n-butoxy, isobutoxy or tert-butoxy. When Y is alkyl, aryl or aralkyl substituted with at least one halogen, the halogen is preferably fluorine, chlorine or bromine.

Among the preferred compounds of the invention are those wherein X is hydrogen or fluorine or trifluoromethyl, those in which Y is hydrogen, those in which Y is alkyl of 1 to 6 carbon atoms, for example methyl, isopropyl or tert-butyl, those in which Y is $Si(Alk_1)_3$ in which $Alk_1$ has the previous meaning, for example methyl.

Among the preferred compounds are those in which the geometry of the double bond is cis.

Other preferred compounds of Formula I are those wherein R is selected from the group consisting of a) alkyl of 1 to 18 carbon atoms, b) benzyl optionally substituted by at least one member of the group consisting of halogen, alkyl, alkenyl, alkynyl, cycloalkyl, —O alkyl, —O alkenyl, —O alkynyl, —Salkyl, —Salkenyl and —Salkynyl, all containing up to 8 carbon atoms and optionally substituted by at least one halogen, —$NO_2$, +CN and —$NH_2$,

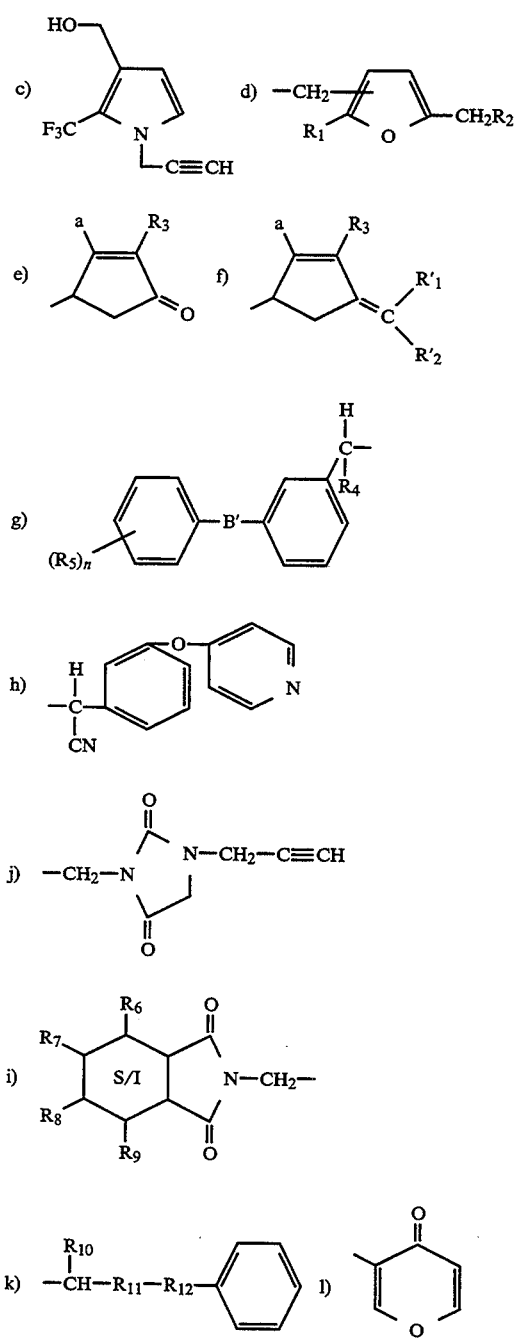

-continued n) 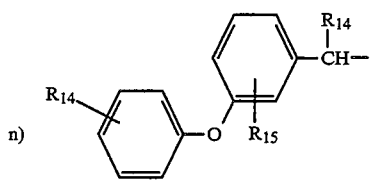

m) 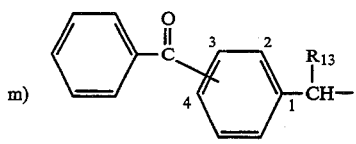

o) 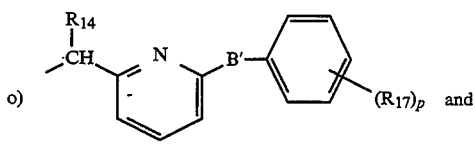

p) 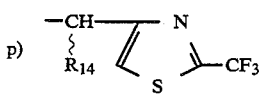

$R_1$ is hydrogen or methyl, $R_2$ is monocyclic aryl or —$CH_2$—C≡CH, a is hydrogen or methyl, $R_3$ is aliphatic of 2 to 6 carbon atoms with at 6 least one carbon-carbon unsaturation, $R'_1$ and $R'_2$ are individually selected from the group consisting of hydrogen, halogen, alkyl of 1 to 6 carbon atoms, —CN, aryl of 6 to 10 carbon atoms and alkoxy carbonyl of 2 to 5 carbon atoms, B' is selected from the group consisting of —O—, —S—,

—$CH_2$, sulfoxide and sulfone, $R_4$ is selected from the group consisting of hydrogen, —CN, methyl, —$CONH_2$, —$CSNH_2$ and —C≡CH, $R_5$ is halogen or methyl, n and p are 0 or 1 or 2, $R_6$, $R_7$, $R_8$ and $R_9$ are individually hydrogen or chlorine or methyl, S/I symbolizes aromatic ring or dihydro or tetrahydro aromatic ring, $R_{10}$ is hydrogen or —CN, $R_{12}$ is —$CH_2$— or —O—, $R_{11}$ is thiazolyl or thiadiazolyl with the bond to

—CH—
|
$R_{10}$ in any available position and $R_{12}$ is linked to $R_{11}$ by the carbon atom between the sulfur and nitrogen atoms, $R_{13}$ and $R_{14}$ are individually selected from the group consisting of hydrogen, methyl, ethynyl and —CN with the benzyl in position 3- or 4-, $R_{15}$ and $R_{16}$ are different and are selected from the group consisting of hydrogen, fluorine and bromine, B" is —O— or —S— and the $R_{17}$s are individually selected from the group consisting of alkyl, alkoxy, alkylthio and alkylsulfonyl of 1 to 4 carbon atoms, 3,4-methylenedioxy, chloro, fluoro and bromo.

Especially preferred compounds of Formula I are those where R is

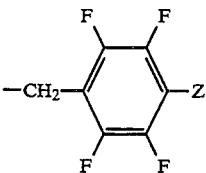

wherein Z is hydrogen, fluorine, NH2, cycloalkyl, alkyl, alkenyl or alkynyl, O-alkyl, O-alkynyl, S-alkyl and S-alkenyl of up to 8 carbon atoms, optionally substituted by at least one halogen, preferably fluorine. Among the preferred values of Z are H, F, $CH_3$, $CF_3$, $OCF_3$, $OCHF_2$, $CH_2C$≡CH and $CH_2$—CH=$CH_2$.

Among the preferred compounds of Formula I are those wherein R is

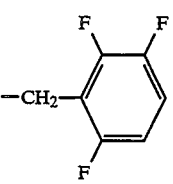

The most preferred compounds are those of Examples 1, 14, 22, 29, 30, 35, 39, 40, 54 and 55.

The most preferred compounds are those of Examples 33, 35, 43 and 45.

The process for the preparation of a compound of Formula I comprises reacting an acid or a functional derivative thereof of the formula

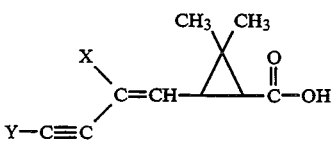

in which X and Y have the above definitions with an alcohol of the Formula

ROH                                III in which R has the above definition or a functional derivative of the alcohol to obtain the corresponding compound of Formula I.

The esterification of the acid of Formula II with the alcohol of Formula III can be carried out in the presence of a tertiary base such as pyridine and can be advantageously carried out in the presence of a mixture of pyridine, dicyclohexylcarbodiimide and 4-dimethylamino-pyridine. The esterification can also be carried out by reacting a chloride of acid II on the alcohol of Formula III or on a metallic derivative of the alcohol such as a silver salt.

The compounds of Formula II used as starting products for the process of the invention are new products and are in themselves a subject of the present invention. Detailed examples of the preparation of the compounds of Formula II are given hereafter in the experimental part, their preparation can be schematized as follows:

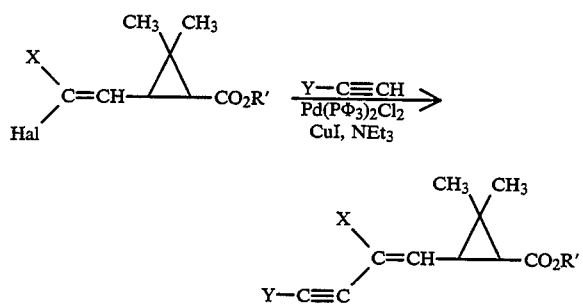

R′ is alkyl of 1 to 18 carbon atoms or a remainder of an acid used in the pyrethrinoid series and Hal is bromine or chlorine or iodine

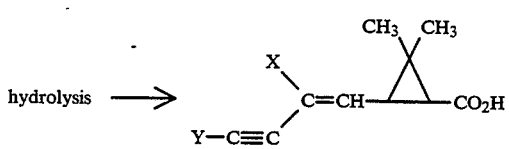

If desired, the stereoisomers obtained are separated.

In a variant of the previous process, a compound of the formula

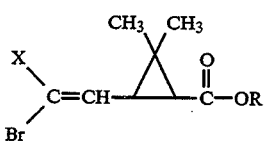

is subjected to the action of an agent capable of replacing bromine by C≡CY to obtain the corresponding compound of Formula I.

The novel pesticidal compositions of the invention are comprised of a pesticidally effective amount of at least one compound of Formula I and an inert carrier. They are useful for combatting parasites of vegetation of the soil or the above ground plants, parasites of premises and parasites of warm-blooded animals.

Thus, it is that the products of the invention can be used for combatting parasitic insects, nematodes and acaridae of vegetation and animals.

A particular subject of the invention is the use of the compounds of Formula I for combatting parasites of warm-blooded animals.

The products of Formula I can also be used for combatting insects and other parasites of the soil, for example Coleoptera, such as DIABROTICA, click beetles and May beetle grubs, Myriapoda such as scutigeridae and blanjules, and Diptera such as cecydomia and Lepidoptera such as owlet moths.

They are used at doses comprised between 10 g and 300 g of active ingredient per hectare.

The products of Formula I can also be used for combatting insects in premises, for combatting in particular flies, mosquitoes and cockroaches.

The products of Formula I are more photostable and are not very toxic to mammals.

All of these properties makes the products of Formula I products which correspond perfectly to the requirements of the modern agrochemical industry; they allow crops to be protected while preserving the environment.

The products of Formula I can also be used for combatting parasitic acaridae and nematodes of vegetation.

The compounds of Formula I can also be used for combatting parasitic acaridae of animals, for combatting for example ticks and notably ticks of the Boophilus species, those of the Hyalomnia species, those of the Amblyomnia species and those of the Rhipicephalus species, or for combatting all sorts of mites and notably the sarcoptic mite, the psoroptic mite and the chorioptic mite.

Therefore, a subject of the invention is the composition intended for combatting parasites of warm-blooded animals, parasites of premises and of vegetation, characterized in that they contain at least one of the products of Formula (I) defined above, notably the products of Examples 1, 14, 22, 29, 30, 39, 40 and 41 or also those of Examples 54 and 55 and quite particularly those of Examples 33, 35, 43 and 45.

Among the products of formula (I) der ined above, there can be mentioned more especially as products intended for combating Diabrotica, the products for combating Blatella, the products of Examples 22, 32, 34, 48, 49, 50, 51 and 52, as products intended for combating Lepidoptera, the products of Examples 46 and 47 and as products intended for combating Aphids, there can be mentioned more especially the products of Examples 1, 47 and 53.

A particular subject of the invention is the insecticide compositions containing as active ingredient at least one of the products defined above.

These compositions are prepared according to the usual processes of the agrochemical industry or the veterinary industry or the animal nutrition products industry.

In those compositions intended for agricultural use and for use in premises, the active ingredient or ingredients can optionally have added to them one or more other pesticide agents. These compositions can be presented in the form of powders, granules, suspensions, emulsions, solutions, aerosol solutions, combustible strips, baits or other preparations usually employed for the use of this type of compound.

In addition to the active ingredient, these compositions contain, in general, a vehicle and/or a non-ionic surfactant, ensuring, moreover, a uniform dispersion of the constitutive substances of the mixture. The vehicle used can be a liquid, such as water, alcohol, hydrocarbons or other organic solvents, a mineral, animal or vegetable oil, a powder such as talc, clays, silicates, kieselguhr or a combustible solid.

The insecticide compositions according to the invention preferably contain 0.005% to 10% by weight of active ingredient.

According to an advantageous operating method, for use in premises, the compositions according to the invention are used in the form of fumigant compositions.

The compositions according to the invention can therefore be advantageously constituted, for the non-active part, of a combustible insecticide coil, or also of an incombustible fibrous substrate. In the latter case, the fumigant obtained after incorporation of the active ingredient is placed on a heating apparatus such as an electric. emanator.

In the case where an insecticide coil is used, the inert support can be, for example, composed of pyrethrum marc, Tabu powder (or Machilus Thumbergii leaf powder), pyrethrum stem powder, cedar leaf powder, sawdust (such as of pine sawdust), starch and coconut shell powder.

The dose of active ingredient can then be, for example, 0.03 to 1% by weight.

In the case where an incombustible fibrous support is used, the dose of active ingredient can then be, for example, 0.03 to 95% by weight.

The compositions according to the invention for use in premises can also be obtained by preparing a sprayable oil based on the active ingredient, this oil soaking the wick of a lamp and then being set alight.

The concentration of active ingredient incorporated in the oil is, preferably, 0.03 to 95% by weight.

Also a subject of the invention is the acaricide compositions containing as active ingredient at least one of the products of formula I defined above.

The insecticide compositions according to the invention, as acaricide and nematicide compositions, can optionally have added to them one or more other pesticide agents. The acaricide and nematicide compositions can be presented in particular in the form of powder, granules, suspensions, emulsions, solutions.

For acaricide use, wettable powders are preferably used for foliar spraying, containing 1 to 80% by weight of active ingredient, or liquids for foliar spraying containing 1 to 500 g/l of active ingredient. Powders can also be used for foliar dustings containing 0.05 to 3% of active ingredient.

For nematicide use, liquids for soil treatment are preferably used containing 300 to 500 g/l of active ingredient.

The acaricide and nematicide compositions according to the invention are used, preferably, at doses comprised between 1 and 100 g of active ingredient per hectare.

In order to enhance the biological activity of the products of the invention they can have added to them standard synergists used in such cases such as 1-(2,5,8-trioxadodecyl ) 2-propyl 4,5-methylenedioxy benzene (or piperonyl butoxide) or N-(2-ethyl heptyl) bicyclo[2,2-1]hept-5-ene-2,3-dicarboximide, or piperonyl-bis-2- (2'-n-butoxy ethoxy) ethylacetal ( or tropital ).

The compounds of formula (I) have an excellent general tolerance, and therefore a subject of the invention is also the products of formula (I), for combating in particular illnesses caused by ticks and mites in man and animals.

The products of the invention are notably used for combating lice in a preventative or curative manner and for combating scabies.

The products of the invention can be administered externally, by spraying, by shampooing, by bathing or painting-on.

The products of the invention for veterinary use can also be administered by painting on the spine according to the so-called "pour-on" method.

It can also be indicated that the products of the invention can be used as growth regulators.

Also a subject of the invention is the combinations endowed with insecticide, acaricide or nematicide activity, characterized in that they contain as active ingredient, on the one hand at least one of the compounds of general formula (I), and on the other hand, at least one of the pyrethrinoid esters chosen from the group constituted by the esters of allethrolone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcoholswith chrysanthemic acids, by the esters of 5-benzyl-3-furyl methyl alcohol with 2,2-dimethyl-3-(2-oxo-3-tetrahydrothiophenylidenemethyl)-cyclopropane-1-carboxylic acids, by the esters of 3-phenoxybenzyl alcohol and of alpha-cyano-3-phenoxybenzyl alcohol with 2,2-dimethyl-3-(2,2-dichlorovinyl)-cyclopropane-1-carboxylic acids, by the esters of alpha-cyano-3phenoxy-benzyl alcohol with 2,2-dimethyl-3-(2,2-dibromovinyl)-cyclopropane-1-carboxylic acids, by the esters of 3alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of alpha-cyano-3-phenoxybenzyl alcohol with 2,2-dimethyl-3-( 1,2,2,2-tetrahaloethyl) -cyclopropane-1-carboxylic acids, in which "halo" represents a fluorine, chlorine or bromine atom, it being understood that the compounds (I) can exist in all their possible stereoisomer forms, as well as the acid and alcohol copulas of the above pyrethrinoid esters.

The following examples illustrate the invention without however limiting it.

EXAMPLE I 2,3,5,6-tetrafluoro-4-2-propynyl) phenylmethyl [1R-[1alpha, 3alpha (Z)]] 2,2-dimethyl 3-[4-(trimethylsilyl) but-1-en-3-ynyl] cyclopropanecarboxylate A solution of 1.75 g of dicyclohexylcarbodiimide and 3 cm$^3$ of methylene chloride is added at 0°/+5° C. to a solution containing 2.12 g of [1R-[1alpha, 3alpha(Z)]] 2,2-dimethyl-3-[4-(trimethylsilyl) but-1-en-3-ynyl] cyclopropane carboxylic acid, prepared as indicated hereafter, 20 cm$^3$ of methylene chloride, 2 g of 2,3,5,6-tetrafluoro 4-(2-propynyl) benzyl alcohol and 20 mg of dimethylamino pyridine. The reaction mixture is maintained under agitation for one hour at 0°/+5° C. then for 2 hours at 20° C. After filtering, the filtrate is rinsed and concentrated. 4.53 g of product is obtained which is chromatographed on silica, eluting with a hexane—methylene chloride mixture (70–30). 1.34 g of the desired product is obtained, rf=0.23.

[alpha]$_D$=117.50 (c=1% CHCl$_3$).

PREPARATION 1

[1R-[1alpha, 3alpha(Z) ]] 2,2-dimethyl 3-[4-(trimethylsilyl) but-1-en-3-ynyl] cyclopropanecarboxylic acid 3.47 g of chlorotrimethylsilane is added at 15° C. to a mixture of 6.75 g of [1R-[1alpha, 3alpha(Z)]] 3-[2-bromo ethenyl] 2,2-dimethyl cyclopropanecarboxylic acid, obtained according to EP 0381563, 70 cm$^3$ of methylene chloride and 2.31 g of imidazole. The reaction mixture is maintained under agitation for one hour 30 minutes at 20° C., then it is filtered and the filtrate is brought to dryness. 7.37 g of product is obtained to which is added 110 cm$^3$ of anhydrous triethylamine and 7 cm$^3$ of trimethylsilylacetylene. The reaction mixture is maintained under agitation while adding at 20° C., 0.91 g of bis(triphenylphosphine) palladium dichloride and 0.16 g of copper iodide. The reaction mixture is maintained under agitation for 5 hours at 45° C., then for 16 hours at 20° C. It is filtered and the filtrate is brought to dryness. 100 cm$^3$ of a saturated aqueous solution of sodium acid phosphate is added. Extraction is carried out with isopropyl ether. The organic phases are united, dried, filtered and brought to dryness. 9.4 g of product is obtained which is chromatographed on silica, eluant toluene—ethyl acetate—acetic acid (95-5-0.1). In this way the desired product is isolated. rf=0.16.

EXAMPLE 2

(pentafluorophenyl) methyl [1R-[1alpha, 3alpha(E)]] 2,2-dimethyl 3-[4-(trimethylsilyl) but-1-en-3-ynyl]cyclopropanecarboxylate By operating as in Example 1, starting with [1R-[1alpha, 3alpha(E) ]] 2,2-dimethyl 3-[4-(trimethylsilyl) but-1-en-3-ynyl] cyclopropanecarboxylic acid prepared as indicated hereafter and pentafluorobenzyl alcohol, the desired product is obtained, melting at 9° C.

PREPARATION 2

[1R-[1alpha, 3alpha(E) ]] 2,2-dimethyl 3-[4-(trimethylsilyl) but-1-en-3-ynyl] cyclopropanecarboxylic acid By operating as in Preparation 1, starting with [1R-[1alpha, 3alpha(E)]] 3-(2-bromo ethenyl) 2,2-dimethyl cyclopropanecarboxylic acid obtained according to EP 0381563, the desired product is obtained.

EXAMPLES 3 To 13

By operating as in Example 1, starting with [1R-[1alpha, 3alpha(Z)]] 2,2-dimethyl 3-[4-(trimethylsilyl) but-1-en-3-ynyl] cyclopropanecarboxylic acid (Preparation 1) or

[1R-[1alpha, 3alpha(E) ]] 2,2-dimethyl 3-[2-fluoro 4-(trimethylsilyl) but-1-en-3-ynyl ] cyclopropanecarboxylic acid (Preparation 3 ) and the appropriate alcohol, the following products were prepared:

EXAMPLE 3

[2-fluoro 6-(trifluoromethyl)phenyl] methyl [1R-[1alpha, 3alpha(Z)]] 2,2-dimethyl 3-[4-(trimethylsilyl) but-1-en-3-ynyl] cyclopropanecarboxylate, M.p.=39.5°.

EXAMPLE 4

[(4-difluoromethoxy) 2,4,5,6-tetrafluoro phenyl] methyl [1R-[1alpha, 3alpha(Z)]] 2,2-dimethyl 3-[4-(trimethylsilyl) but-1-en-3-ynyl] cyclopropanecarboxylate, rf=0.13, eluant: hexane—isopropyl ether ( 97–3 ).

EXAMPLE 5

[1-(2-propynyl) 2-(trifluoromethyl) 1-pyrrol 2-yl] methyl [1R-[1alpha, 3alpha(Z)]] 2,2-dimethyl 3-[4-(trimethylsilyl) but-1-en-3-ynyl] cyclopropanecarboxylate $[alpha]_D=139°$ (c=1.1% $CHCl_3$).

EXAMPLE 6

[(4-amino 2,3,5,6-tetrafluoro) phenyl] methyl [1R-[1alpha, 3alpha(Z)]] 2,2-dimethyl 3-[4-(trimethylsilyl) but-1-en-3-ynyl] cyclopropanecarboxylate, rf=0.2, eluant: hexane—ethyl acetate (85–15).

EXAMPLE 7

(1,3,4,5,6,7-hexahydro-1,3-dioxo-2H-isoindol-2-yl) methyl [1R-[1alpha, 3alpha(Z)]] 2,2-dimethyl 3-[4-(trimethylsilyl) (but-1-en-3-ynyl) cyclopropanecarboxylate M.p.=87.9°.

EXAMPLE 8

S (3-phenoxy phenyl) cyanomethyl [1R-[1alpha, 3alpha(Z) ]] 2,2-dimethyl 3-[4-(trimethylsilyl) but-1-en-3-ynyl] cyclopropanecarboxylate, M.p.=82.2°.

EXAMPLE 9

(2,3,5,6-tetrafluoro 4-methyl phenyl) methyl [1R-[1alpha, 3alpha(Z)]] 2,2-dimethyl 3-[4-(trimethylsilyl) but-1-en-3-ynyl] cyclopropanecarboxylate, rf=0.23, eluant: hexane—methylene chloride (70-30).

EXAMPLE 10

(2,3,5,6-tetrafluoro phenyl) methyl [1R-[1alpha, 3alpha(Z) ]] 2,2-dimethyl 3- [4- (trimethylsilyl) but-1-en-3-ynyl] cyclopropanecarboxylate, $[alpha]_D=+137.5°$ (C=1% $CHCl_3$).

EXAMPLE 11

(2,3,5,6-tetrafluoro phenyl) methyl [1R-[1alpha, 3alpha(E) ]] 2,2-dimethyl 3-[2-fluoro 4-(trimethylsilyl) but-1-en-3-ynyl] cyclopropanecarboxylate, rf=approx. 0.13, eluant: hexane 80 $CH_2Cl_{20}$

EXAMPLE 12

(2,6-difluoro phenyl) methyl [1R-[1alpha, 3alpha (E)]] 2,2-dimethyl 3-[2-fluoro 4- (trimethylsilyl) but-1-en-3-ynyl] cyclopropanecarboxylate, rf=0.18, eluant: hexane 97 isopropyl ether 3

EXAMPLE 13

(2,3,6-trifluoro phenyl) methyl [1R-[1alpha, 3alpha(E)]] 2,2-dimethyl 3-[2-fluoro 4-(trimethylsilyl) but-1-en-3-ynyl] cyclopropanecarboxylate, rf=0.16 eluant: hexane 80 $CH_2Cl_{20}$

PREPARATION 3

[1R-[1alpha, 3alpha(E)]] 2,2-dimethyl 3-[2-fluoro 4-(trimethylsilyl) but-1-en-3-ynyl] cyclopropane-carboxylic acid, By operating as in Preparation 1, starting with 14.6 g of [1R-[1alpha, 3alpha(Z)]] 3-[2-bromo 2-fluoro ethenyl] 2,2-dimethyl cyclopropanecarboxylic acid obtained according to EP 0378026, 10.56 g of desired product is obtained. rf=0.10, eluant: hexane 90 ACOEt 10 ACOH 1.

PREPARATION 4

2,3,6-trifluoro benzyl alcohol 10.56 g of 2,3,6-trifluoro benzoic acid is dissolved at ambient temperature in 100 $cm^3$ tetrahydrofuran. The solution is cooled down in an ice-methanol bath and a solution containing 10 $cm^3$ of borane methyl sulphide complex at 10 millimoles/$cm^3$ and 30 $cm^3$ of tetrahydrofuran is added over 30 minutes. Agitation is carried out for 5 minutes and the mixture is left to return to ambient temperature. After heating for 3 hours 30 minutes at 45°/50° C., the solution obtained is poured into an aqueous solution of sodium acid phosphate. Extraction is carried out with isopropyl ether, the extracts are washed, dried and brought to dryness. 10.6 g of a colourless liquid is obtained which is chromatographed on silica, eluting with a hexane—ethyl acetate mixture (7–3). 8.8 g of desired product is obtained. M.p.<50° C.

IR Spectrum (CHCl$_3$)
OH: 3620 cm$^{-1}$
Aromatic: 1642, 1604, 1499 cm$^{-1}$
NMR Spectrum: (CDCl$_3$, 60 Hz) ppm
Aromatic protons: 6.70–7.47
C$\underline{H}_2$—OH: 4.83
O$\underline{H}$: 2.20

EXAMPLE 14

(2,3,5,6-tetrafluoro 4-methyl phenyl) methyl [1R-[1alpha, 3alpha(Z)]] 3-(2-fluoro 5,5-dimethyl hex-1-en-3-ynyl) 2,2-dimethyl cyclopropanecarboxylate and its corresponding (E) isomer.

A mixture of 2 g of 4-methyl tetrafhorobenzyl [1R-[1alpha, 3alpha(E+Z) ]] 3-(2-bromo 2-fluoro ethenyl) 2,2-dimethyl cyclopropanecarboxylate obtained according to EP 0381563, 0.720 cm$^3$ of 3,3-dimethyl 1-butyne, 20 cm$^3$ of triethylamine, 170 mg of bis(triphenylphosphine) palladium dichloride and 26 mg of copper iodide is maintained under agitation for 20 hours at 45°/50° C. The reaction medium is poured into a water and ice mixture. Extraction is carried out with ethyl acetate, the extracts are dried and concentrated to dryness. The product obtained is chromatographed on silica, eluting with a hexane - methylene chloride mixture (7–3). 1.13 g of desired product is obtained, E isomer, M.p.=47° C. (rf=0.20) [alpha]$_D$=+108.5° (C=1.1% CHCl$_3$) and 0.7 g of Z isomer: rf=0.27 [alpha]$_D$=–77° (C=0.6% CHCl$_3$)

EXAMPLES 15 to 21

By operating as in the previous example, and following the reaction diagram:

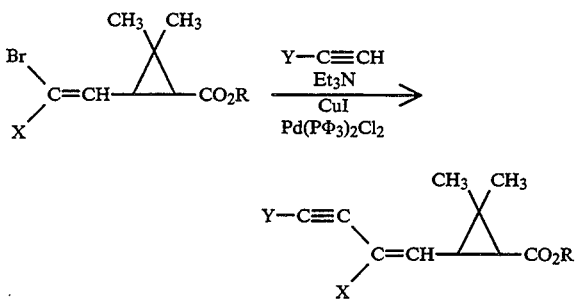

the following products were obtained:

EXAMPLE 15

(2,3,5,6-tetrafluoro 4-methyl phenyl) methyl [1R-1alpha, 3alpha(Z)]] 3-(2-fluoro pent-1-en-3-ynyl) 2,2-dimethyl cyclopropanecarboxylate M.p.=84° C. and corresponding E isomer (Rf 0.24 Hexane 7—CH$_2$Cl$_2$ 3)

EXAMPLE 16

(2,3,5,6-tetrafluoro 4-methyl phenyl) methyl [1R-[1alpha, 3alpha(E) ]] 3-(2-fluoro hex-1-en-3-ynyl) 2,2-dimethyl cyclopropanecarboxylate Rf 0.28 (Hexane 7—methylene chloride 3) and corresponding Zisomer.

EXAMPLE 17

(2,3,5,6-tetrafluoro 4-methyl phenyl) methyl [1R-[1alpha, 3alpha(E)]] 3-(2-fluoro 4-phenyl but-1-en-3-ynyl) 2,2-dimethyl cyclopropanecarboxylate

[alpha]$_D$=+191.5° (0.75% CHCl$_3$)

EXAMPLE 18

(pentafluorophenyl) methyl [1R-[1alpha, 3alpha(E)]] 3-(2-fluoro 4-trimethylsilyl but-1-en-3-ynyl) 2,2-dimethyl cycopropanecarboxylate Starting with pentafluorobenzyl [1R-[1alpha, 3alpha(E+Z)]] 3-(2-bromo 2-fluoroethenyl ) 2,2-dimethyl cyclopropanecarboxylate obtained according to EP 0381563, the expected product was obtained.

[alpha]$_D$=+106° (2.2% CHCl$_3$) and the corresponding Z isomer [alpha]$_D$=–89° (1.1% CHCl$_3$)

EXAMPLE 19

(2,3,5,6-tetrafluoro 4-methyl phenyl) methyl [1R-[1alpha, 3alpha (Z)]]3-[2-fluoro 4-(trimethylsilyl) but-1-en-3-ynyl] 2,2-dimethyl cyclopropanecarboxylate M.p.<50° C. and the corresponding E isomer.

EXAMPLE 20

(2,3,5,6-tetrafluoro 4-methyl phenyl) methyl [1R-[1alpha, 3alpha(Z)]] 3-[2-fluoro 5-(trimethylsilyl) pent-1-en-3-ynyl] 2,2-dimethyl cyclopropanecarboxylate,

[alpha]$_D$=–93.5° (0.7% CHCl$_3$) and the corresponding(E) isomer [alpbal]$_D$=+140° (0.7% CHCl$_3$)

EXAMPLE 21

(2,3,5,6-tetrafluoro 4-methyl phenyl) methyl [1R-[1alpha, 3alpha(Z)]] 2,2-dimethyl 3-(4-phenyl but-1-en-3-ynyl) cyclopropanecarboxylate, Starting with 4-methyl tetrafluorobenzyl [1R-[1alpha, 3alpha(Z) ]] 3-(2-bromoethenyl) 2,2-dimethyl cyclopropane-carboxylate obtained according to EP 0381563, the expected product was obtained.

[alpha]$_D$=+199° (C=1% CHCl$_3$).

EXAMPLE 22

[2,3,5,6-tetrafluoro 4-(2-propynyl) phenyl] methyl [1R-[1alpha, 3alpha(Z) ]] 3-(but-1-en-3-ynyl) 2,2-dimethyl cyclopropanecarboxylate 1.37 g of potassium fluoride is added at 0°+5° C. to a solution containing 2.04 g of the product of Example 1, 20 cm$^3$ of methanol and 0.47 cm$^3$ of acetic acid. The mixture is agitated for 5 minutes at 0°+5° C. then for 16 hours at 20° C. After concentrating, the resultant product is taken up in water and extracted with isopropyl ether. The extracts are dried, filtered and brought to dryness. 1.85 g of a product is obtained which is chromatographed on silica, eluting with a hexane—isopropyl ether mixture (97–3). 0.913 g of the desired product is obtained. M.p.=61° C.

By operating as in Example 22, and by following the reaction diagram:

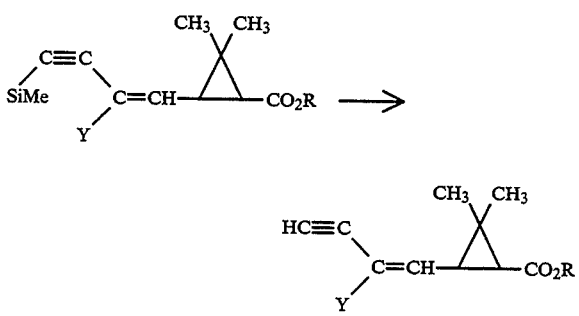

the following products were obtained:

EXAMPLE 23

[2-fluoro 6-(trifluoromethyl) phenyl] methyl [1R-[1alpha, 3alpha(Z)]] 3-(but-1-en-3-ynyl) 2,2-dimethyl cyclopropanecarboxylate Using 1.83 g of the product obtained in Example 3, 1.19 g of the desired product was obtained.
rf=0.5
Eluant: hexane—isopropyl ether (95–5).

EXAMPLE 24

[2,3,5,6-tetrafluoro 4-(difluoromethoxy) phenyl]methyl [1R-[1alpha, 3alpha(Z)]] 3-(but-1-en-3-ynyl) 2,2-dimethyl cyclopropanecarboxylate Starting with 1.43 g of the product obtained in Example 4, 1.02 g of the desired product was collected.
rf=0.2
Eluant: hexane—isopropyl ether (95–5).

EXAMPLE 25

[1-(2-propynyl) 2-(trifluoromethyl) 1-pyrrol-3-yl] methyl [1R-[1alpha, 3alpha(Z)]] 3-(but-1-en-3-ynyl) 2,2-dimethyl cyclopropanecarboxylate Starting with 1.1 g of the product obtained in Example 5, 0.83 g of the desired product was obtained.
rf=0.13
Eluant: hexane—isopropyl ether (97–3).

EXAMPLE 26

(pentafluorophenyl) methyl [1R-[1alpha 3alpha (E)]] 3-(but-1-en-3-ynyl) 2,2-dimethyl cyclopropane-carboxylate Starting with 2.28 g of the product obtained in Example 2, 1.4 g of the desired product was obtained.
[alpha]$_D$= −90° (C=1% CHCl$_3$).

EXAMPLE 27

(2,3,5,6-tetrafluoro 4-methyl phenyl) methyl [1R-([1alpha, 3alpha(Z) ]] 3-(2-fluoro but-1-en-3-ynyl) 2,2-dimethyl cyclopropanecarboxylate Starting with 1.5 g of the product collected in Example 19 (Z isomer), 1.24 g of the desired product was prepared. (M.p.=58° C.).

EXAMPLE 28

(2,3,5,6-tetrafluoro 4-methyl phenyl) methyl [1R-[1alpha, 3alpha(Z) ]] 3-(but-1-en-3-ynyl) 2,2-dimethyl cyclopropanecarboxylate Starting with 1.5 g of the product of Example 9, 1.1 g of the desired product was obtained.
rf=0.2, eluant: hexane—isopropyl ether (97–3).

EXAMPLE 29

(pentafluorophenyl) methyl [1R-[1alpha, 3alpha(E)]] 3-(2-fluoro but-1-en-3-ynyl) 2,2-dimethyl cyclopropanecarboxylate Starting with 1.24 g of the product of Example 18 (E isomer), 990 mg of the desired product was obtained.
[alpha]$_D$= +89° (C=1.6% CHCl$_3$).

EXAMPLE 30

(2,3,5,6-tetrafluoro 4-methyl phenyl) methyl [1R-[1alpha, 3alpha(E) ]] 3-(2-fluoro but-1-en-3-ynyl) 2,2-dimethyl cyclopropanecarboxylate Starting with 4.1 g of the product of Example 19 (E isomer), 3.36 g of the desired product was obtained.
M.p.<50° C.
rf=0.23, eluant: hexane—methylene chloride (7–3).

EXAMPLE 31

(pentafluoropheny)l methyl [1R-[1alpha, 3alpha (Z)]] 3-(2-fluoro but-1-en-3-ynyl) 2,2-dimethyl cyclopropanecarboxylate Starting with 1 g of the product of Example 18 (Z isomer), 840 mg of the desired product was obtained.
M.p.=approx. 57° C.
[alpha]$_D$= −66° (C=1% CHCl$_3$)

EXAMPLE 32

(4-amino 2,3,5,6-tetrafluoro phenyl) methyl [1R-1alpha, 3alpha(Z) ]] 3-(but-1-en-3-ynyl) 2,2-dimethyl cyclopropanecarboxylate Starting with 2.11 g of the compound of Example 6, 1.4 g of the desired product was obtained.
M.p.=80.20C.

By operating starting with the compounds obtained in Examples 11 to 13 according to the operating method indicated in Example 22, the products of Examples 33 to 35 respectively were obtained.

EXAMPLE 33

(2,3,5,6-tetrafluoro phenyl) methyl [1R-[1alpha, 3alpha(E) ]] 2,2-dimethyl 3-(2-fluoro but-1-en-3-ynyl) cyclopropanecarboxylate rf=0.18 cyclohexane—methylene chloride 7–3.

EXAMPLE 34

(2,6-difluoro phenyl) methyl [1R-[1alpha, 3alpha (E)]] 2,2-dimethyl 3- (2-fluoro but-1-en-3-ynyl) cyclopropanecarboxylate rf=0.18 cyclohexane—methylene chloride 7–3.

EXAMPLE 35

(2,3,6-trifluoro phenyl) methyl [1R-[1alpha, 3alpha(E) ]] 2,2-dimethyl 3-(2-fluoro but-1-en-3-ynyl) cyclopropanecarboxylate rf=approx. 0.2, eluant: hexane 70 CH$_2$Cl$_2$ 30.

EXAMPLE 36

(2,3,5,6-tetrafluoro phenyl) methyl [1R-[1alpha, 3alpha (Z)]] 3-(but-1-en-3-ynyl) 2,2-dimethyl cyclopropanecarboxylate 60 cm³ of tetrabutylammonium fluoride, of a molar solution in tetrahydrofuran, is added at 0° C. to a solution containing 2.44 g of the product prepared in Example 10 and 30 cm³ of methylene chloride. The reaction mixture is maintained under agitation for 30 minutes at 0° C. and the temperature is allowed to rise to 15° C. The reaction medium is poured into a saturated aqueous solution of sodium acid phosphate and the whole is agitated for 10 minutes. Extraction is carried out with isopropyl ether. The organic phases are united, dried, filtered and brought to dryness. 1.96 g of a product is obtained which is chromatographed on silica, ehting with a hexane —isopropyl ether mixture (98-2). In this way 1.20 g of the desired product is isolated. (rf=0.16).

[alpha]$_D$= +105.5° (C=0.75% CHCl$_3$).

EXAMPLE 37

(pentafluorophenyl) methyl [1R-[1alpha, 3alpha(Z)]] 2,2-dimethyl 3-[4-(trimethylsilyl) but-1-en-3-ynyl] cyclopropanecarboxylate The product was obtained according to the operating method of Example 14 starting with 2,3,4,5,6-pentafluoro-phenyl methyl [iR-[1alpha, 3alpha]] 2,2-dimethyl 3-(2-bromoethenyl) cyclopropane carboxylate obtained according to EP 0381563.

[alpha]$_D$= +113.5° (C=0.45% CHCl$_3$).

EXAMPLE 38

(pentafluorophenyl) methyl [1R-[1alpha, 3alpha(Z)]] 3-(but-1-en-3-ynyl) 2,2-dimethyl cyclopropane-carboxylate The product was obtained from Example 37 by following the operating method of Example 36.

[alpha]$_D$= +129° (C=0.95% CHCl$_3$).

EXAMPLE 39

(2,3,5,6-tetrafluoro phenyl) methyl [1R-[1alpha, 3alpha(E) ]] 3-(2-fluoro 5,5-dimethyl hex-1-en-3-ynyl) 2,2-dimethyl cyclopropanecarboxylate The product was obtained according to the operating method of Example 14.

Rf=0.12 (hexane 8—CH$_2$Cl$_2$ 2).

EXAMPLE 40

(pentafluorophenyl) methyl [1R-[1alpha, 3alpha(E)]] 3-(2-fluoro 5,5-dimethyl hex-1-en-3-ynyl) 2,2-dimethyl cyclopropanecarboxylate The product was obtained according to the operating method of Example 14.

Rf=0.16 (hexane 8—CH$_2$Cl$_2$ 2).

EXAMPLE 41

[(2,3,5,6-tetrafluoro 4-methyl) phenyl] methyl [1R-[1alpha, 3alpha(E)]] 3-(2-fluoro 5-methyl hex-1-en-3-ynyl) 2,2-dimethyl cyclopropanecarboxylate Rf=0.22 (hexane 8—CH$_2$Cl$_2$ 2).

EXAMPLE 42

(2,3,6-trifluorophenyl) methyl [1R-[1alpha, 3alpha(E)]] 3-(2-trifluoromethyl) 4-(trimethylsilyl) but-1-en-3-ynyl) 2,2-dimethyl cyclopropanecarboxylate By operating as in Example 1 starting with [1R-[1alpha, 3alpha(E) ]] 2,2-dimethyl 3-[2-(trifluoromethyl) 4-(trimethylsilyl) but-1-en-3-ynyl] cyclopropane carboxytic acid and the appropriate alcohol, the expected product is obtained.

PREPARATION 5

[1R-[1alpha, 3alpha(E) ]] 2,2-dimethyl-3-[2-(trifluoromethyl) 4-(trimethylsilyl) but-1-en-3-ynyl] cyclopropane carboxylic acid By operating as in Preparation 1 starting with [1R-[1alpha, 3alpha(E)]] 3-[2-bromo 2-(trifluoromethyl)] ethenyl cyclopropane carboxylic acid obtained according to the European Patent 010874 or the French Patent 2,392,964, the desired product is obtained.

EXAMPLE 43

(2,3 6-trifluorophenyl) methyl [1R-[1alpha, 3alpha(E)]] 3-(2-trifluoromethyl) but-1-en-3-ynyl) 2,2-dimethyl cyclopropane carboxylate.

By operating as in Example 22 starting with the product obtained in Example 42, the expected product is obtained. M.p.=48° C.

EXAMPLE 44

(2,3,5,6-tetrafluorophenyl) methyl [1R-[1alpha, 3alpha(E)]] 3-(2-trifluoromethyl) 4-(trimethylsilyl-but-1-en-3-ynyl) 2,2-dimethyl cyclopropane-carboxylate.

By operating as in Example 42 starting with the acid obtained in Preparation 5 and the appropriate alcohol, the expected product is obtained.

EXAMPLE 45

(2,3,5,6-tetrafluorophenyl) methyl [1R-[1alpha, 3alpha(E) ]] 3-(2-trifluoromethyl) but-1-en-3-ynyl) 2,2-dimethyl cyclopropane carboxylate.

By operating as in Example 43 starting with the product obtained in Example 44, the expected product is obtained. M.p.=63.2° C.

EXAMPLE 46 cyano (3-phenoxyphenyl) methyl [1R-[1alpha (S*), 3alpha(Z)]] 3-(2-fluoropent-1-en-3-ynyl) 2,2-dimethyl cyclopropane carboxylate.

By operating as in Example 1 starting with [1R-[(1alpha, 3alpha(Z)]] 2,2-dimethyl 3-[2-fluoroethenyl pent-1-en-3-ynyl] cyclopropane carboxylic acid and the appropriate alcohol, the expected product is obtained.

PREPARATION 6

[1R-[(1alpha, 3alpha(Z)]] 2,2-dimethyl 3-[2-fluoroethenyl pent-1-en-3-ynyl] cyclopropane carboxylic acid 7.3 g of [1R-[(1alpha, 3alpha(Z)] 2,2-dimethyl 3-(2-bromo 2-fluoroethenyl) cyclopropane carboxylic acid obtained according to EP 0378026 in 70 cm³ of methylene chloride is cooled down to +10° C., 2.09 g of imidazole then 4.3 cm³ of chloro trimethylsilane are added. The whole is agitated while allowing it to return to ambient temperature, filtration is carried out, the filtrate is evaporated and 9.25 g of silylated ester is obtained. 20 cm$^3$ of a 14% solution of methyl acetylene in triethylamine is cooled down to −5° C. 50 cm$^3$ of triethylamine 70 cm$^3$ of acetonitrile, 9.25 g of the silylated ester obtained above, 210 mg of his (triphenylphosphine) palladium dichloride and 3 mg of copper iodide are added and the whole mixture is maintained at 60° C. for 4 hours. The reaction medium is poured into a saturated aqueous solution of sodium phosphate, extracted with ethyl acetate, the extracts are dried and evaporated to dryness. 4.1 g of expected product is obtained.

By operating as indicated in the previous examples starting with the appropriate acid and alcohol, the following products are obtained.

EXAMPLE 47 cyano (3-phenoxyphenyl) methyl [1R-[1alpha (S*) 3alpha (E)]] 3-(2-fluoro 4-trimethylsilyl but-1-en-3-ynyl) 2,2-dimethyl cyclopropane carboxylate M.p.=103.3° C.

EXAMPLE 48

[4-(2-propynyl) 2,3,5,6-tetrafluorophenyl) methyl [1R-[1alpha, 3alpha(E)]] 3-(2-fluoro but-1-en-3-ynyl) 2,2-dimethyl cyclopropane carboxylate Rf=approx. 0.13.

EXAMPLE 49

(2,3,5,6-tetrafluorophenyl) methyl [1R-[1alpha, 3alpha (Z)]] 3-(5,5-dimethyl hex-1-en-3-ynyl) 2,2-dimethyl cyclopropane carboxylate Rf=approx. 0.15 (hexane—AcOEt 98–2).

PREPARATION 7

[1R-[1alpha, 3alpha (Z)]] 2,2-dimethyl 3-(5,5-dimethyl hex-1-en-3-yny1) cyclopropane carboxylic acid The operation is carried out as in Preparation 1 starting with [1R-[(1alpha, 3alpha(Z)] 2,2-dimethyl 3-[2-(bromoethenyl)] cyclopropane carboxylic acid obtained according to EP 0381563 and 1-(trimethylsilyl) 1,1-dimethyl 2-butyn and the expected acid is obtained.

EXAMPLE 50

(4-hydroxymethyl 2,3,5,6-tetrafluorophenyl) methyl [1R-[1alpha, 3alpha(Z) ]] 3-(2-fluoro but-1-en-3-ynyl) 2,2-dimethyl cyclopropane carboxylate M.p.=74° C. Rf=0.09 ( eluant CH$_2$Cl$_2$)

EXAMPLE 51 cyano (3-phenoxyphenyl) methyl [1R-[1alpha(S*), 3alpha(E)]] 3-(2-trifluoromethyl but-1-en-3-ynyl) 2,2-dimethyl cyclopropane carboxylate Rf=approx. 0.25 (CH$_2$Cl$_2$—hexane 50–50).

EXAMPLE 52

[1-(2-trifluoromethyl) 4-thiazolyl] 2-propynyl [1R-[1alpha, 3alpha(E)]] 3-(2-trifluoromethyl) but-1-en-3-ynyl) 2,2-dimethyl cyclopropane carboxylate Rf=approx. 0.2 (hexane—CH$_2$Cl$_2$ 7–3 ).

PREPARATION 8 alpha-ethynyl 2-(trifluoromethyl) 4-thiazolyl methanol 11 cm$^3$ of a molar solution of ethynyl magnesium bromide is added to a solution of tetrahydrofuran containing 2 g of 2-(trifluoromethyl) 4-thiazolecarboxaldehyde. The reaction mixture is kept under agitation for 30 minutes at 20°/25° C. then it is poured into an ammonium chloride solution. Extraction is carried out with methylene chloride, the extracts are dried, filtered and brought to dryness. 2.1 g of desired product is obtained.

EXAMPLE 53

[4(2-propynyl) 2,3,5,6-tetrafluorophenyl)] methyl [1R-[1alpha, 3alpha(E)]] 3-(2-fluoro 4-trimethylsilyl but-1-en-3-ynyl) 2,2-dimethyl cyclopropane carboxylate Rf=approx. 0.15 (hexane—CH$_2$Cl$_2$ 7–3 ).

EXAMPLE 54

(2,6-difluorophenyl) methyl [1R-[1alpha, 3alpha(E)]] 3-(2-trifluoromethyl) but-1-en-3-ynyl) 2,2-dimethyl cyclopropane carboxylate

EXAMPLE 55

(2,3-difluorophenyl) methyl [1R-[1alpha, 3alpha(E)]] 3-(2-trifluoromethyl) pent-1-en-3-ynyl) 2,2-dimethyl cyclopropane carboxylatte.

Rf=0.2 hexane—CH$_2$Cl$_2$ 7–3

PREPARATION 9

[1alpha, 3alpha(E)]] 3-(2-trifluoromethyl) pent-1-en-3yny1) 2,2dimethyl cyclopropane carboxylic acid The operation is carried out as in Example 1 starting with the [1R-[( 1alpha, 3alpha(E)]] 3-(2-bromo-2-(trifluoro-methyl)] ethenyl cyclopropane carboxylic acid obtained according to EP 010874 or BF 2,392,964 and 1-(trimethylsilyl) propyn and the expected product is obtained.

EXAMPLE 56

Preparation of a soluble concentrate

A homogeneous mixture is made of:
Product of Example 1: 0.25 g
Piperonyl butoxide : 1.00 g
Tween 80 : 0.25 g
Topanol A : 0.1 g
Water : 98.4 g

EXAMPLE 57

Preparation of an emulsifiable concentrate

The following are intimately mixed:
Product of Example 2: 0.015 g
Piperonyl butoxide : 0.5 g
Topanol A : 0.1 g
Tween 80 : 3.5 g
Xylene : 95. 885 g

EXAMPLE 58

Preparation of an emulsifiable concentrate

A homogeneous mixture is made of:
Product of Example 3: 1.5 g
Tween 80 : 20.00g
Topanol A : 0.1 g Xylene : 78.4 g

EXAMPLE 59

Preparation of granules

Granules were prepared containing 0.1% to 5% of active ingredients.

BIOLOGICAL STUDY

A - Activity on Diabrotica

The test insects are last-stage larvae of Diabrotica. A 9 cm diameter circle of filter paper, placed on the bottom of a Petri dish, is treated with 2 cm³ of an acetone solution of the product to be tested. After drying, 10 larvae per dose are placed on the paper and a mortality check is carried out 24 hours after the treatment.

From a dose of 10 ppm (onwards) most of the products of the invention and in particular those of Examples 33, 35, 43 and 45 have a good activity.

B - Study of the knock-down effect on the housefly

The test insects are 4-day old female houseflies. The operation is carried out by spraying in a Kearns and March chamber using a mixture of acetone (5%) and Isopar L (petroleum solvent) as solvent (quantity of solvent used 2 ml per second). 50 insects per treatment are used. Checks are carried out every minute up to 10 minutes, then after 15 minutes and the KT 50 is determined by the usual methods.

The products of the invention have a good activity.

C - Study of the lethal effect on SpQ.dOptera Littoralis larvae

The tests are carried out by topical application of an acetone solution of the product to be tested, using an Arnold micro manipulator, on the dorsal thorax of the larvae. 15 larvae are used per dose of product to be tested. The larvae used are fourth stage larvae, that is to say about 10 days old when they are bred at 24° C. and 65% relative humidity. After treatment the individual larvae are placed on an artificial nutritional medium (Poitout medium).

The mortality check is carried out 48 hours after treatment.

From a dose of 5 mg/l (onwards) the products of Example 1 and have a good activity.

D - Acaricide study of the compounds of the invention

Bean plants are used having 2 leaves infested with 25 females of Tetranychus Urticae per leaf and put under a ventilated hood under an illuminated ceiling with constant light. The plants are treated with a Fisher gun: 4 ml of toxic solution per plant of a mixture of equal volumes of water and acetone. The leaves are left to dry for 12 hours then the infestation is carried out. Mortality checks are carried out after 80 hours. The dose used is 5 g of product per hl. The lethal concentration 50 (LC 50) is determined. The products of the invention have a good activity.

E - Study of the lethal effect on Aphis cracivora

Adults of 7 days are used and 10 Aphis are used per concentration used. A contact-ingestion method is used. A bean leaf is treated with a Fisher gun and is then placed in a plastic Petri dish on a circle of damp paper. The treatment is carried out using 2 ml of an acetone solution of product to be tested (1 ml per leaf surface). The insect infestation is carried out after the leaf has been dried. The insects are kept in contact with the leaf for one hour. The insects are placed on non-treated leaves and the mortality is checked after 24 hours.

The products of the invention and in particular the products of Examples 1, 47 and 53 have a good activity.

F - Study of the knock-down effect on cockroaches

The test is carried out on 12-week old male cockroaches (Blattella germanica). The operation is carried out by direct spraying in a 13.5 cm diameter glass chamber.

The product is put in solution in Isopar. 0.75 ml of solution is sprayed for 2.5 seconds over 20 cockroaches which have been placed beforehand in the chamber.

The percentage of cockroaches knocked down after 5 minutes at a dose of 100 mm/l is determined.

The products of the invention, in particular the products of Examples 22, 32, 34, 48, 49, 50, 51 and 52, have a good activity.

What is claimed is:

1. A compound of the formula

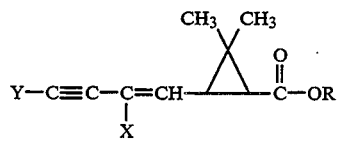

in all possible stereoisomeric forms and mixtures thereof wherein X is selected from the group consisting of hydrogen, halogen and alkyl, alkenyl, alkynyl and cycloalkyl, all having up to 8 carbon atoms and optionally substituted with at least one halogen, Y is selected from the group consisting of a) hydrogen, alkyl, alkenyl, alkynyl and cycloalkyl all having up to 8 carbon atoms optionally substituted iwth at least one member of the group consisting of halogen, —CN, —OH and alkoxy of 1 to 6 carbon atoms, b) phenyl and phenylalkyl of up to 16 carbon atoms optionally substituted with at least one member of the group consisiting of halogen, alkyl of 1 to 8 carbon atoms, alkoxy of 1 to 8 carbon atoms, $-(CH_2)_m-Si(Alk_1)_3$, $-(CH_2)_n-OAlk_2$, $-(CH_2)_p-SAlk_3$, halogen and hydrogen, m, n and p are integers from 0 to 6, $Alk_1$, $Alk_2$ and $Alk_3$ being alkyl or cycloalkyl of up to 8 carbon atoms and R is

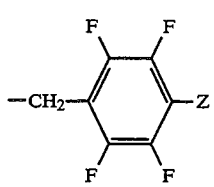

wherein Z is selected from the group conssiting of hydrogen, fluorine, $NH_2$, cycloalkyl, alkyl, alkenyl, alkynyl, O-alkyl, O-alkenyl, S-alkyl or S-alkenyl of up to 8 carbon atoms all optionally substituted by at least one halogen.

2. The compound of claim 1 wherein X is hydrogen or fluorine or —CF₃.

3. A compound of claim 1 wherein Y is hydrogen.

4. A compound of claim 1 wherein Y is alkyl of 1 to 6 carbon atoms.

5. A compound of claim 1 wherein Y is methyl or isopropyl or tert.-butyl.

6. A compound of claim 1 wherein Y is $-Si(Alk_1)_3$.

7. A compound of claim 6 wherein $Alk_1$ is methyl.

8. A compound of claim 1 wherein the double bond geometry is cis.

9. A compound of claim 1 wheren Z is selected from the group consisting of H, F, $CH_3$, $CF_3$, $OCF_3$, $OCHF_2$, $CH_2C\equiv CH$ and $CH_2-CH=CH_2$.

10. A compound of claim 1 selected from the group consisting of [2,3,5 6-tetrafluoro 4-methyl-phenyl)-methyl [1R-[1α, 3α (Z)]] 3-(2-fluoro 5,5-dimethyl hex-1-en-3-ynyl) 2,2-dimethyl cycloppanecarboxylate,

[2,3,5,6-tetrafluoro 4-(2-propynyl) phenyl]-methyl [1R-[1α, 3α (Z)]] 2,2-dimethyl 3-[4-(trimethylsilyl)-but-1-en-3-ynyl] cyclopropanecarboxylate.

[2,3,5,6-tetrafluoro 4- (2-propynyl) phenyl]-methyl [1R- [1α, 3α (Z)]] 3-(but-1-en-3-ynyl) 2,2-dimethyl cyclopropanecarboxylate, (pentafluorophenyl)-methyl [1R-[1α, 3α (E)]] 3-(2-fluoro but-1-en-3-ynyl) 2,2-dimethyl cyclopropanecarboxylate, (2,3,5,6-tetrafluoro 4-methyl phenyl]-methyl [1R-1α, 3α (E)]] 3- ( 2-fluoro but-1-en-3-ynyl) 2,2-dimethyl cyclopropanecarboxylate, (2,3,5,6-tetrafluorophenyl)-methyl [1R-[1α, 3α (E)]] 3-(2-fluoro 5,5-dimethyl hex-1-en-3-ynyl) 2,2-dimethyl cyclopropanecarboxylate, (pentafluorophenyl)-methyl [1R-[1α, 3α (E)]] 3-(2-fluoro 5,5-dimethyl hex-1-en-3-ynyl) 2,2-dimethyl cyclopropanecarboxylate, (2,3,5,6-tetrafluoro 4-methyl phenyl)-methyl [1R-[1α, 3α (E)]] 3- ( 2-fluoro 5-methyl hex-1-en-3-ynyl) 2,2-dimethyl cyclopropane-carboxylate, (2,3,5,6-tetrafluoro phenyl)-methyl [1R-[1α, 3α (E)]] 3-2-fluoro but-1-en-3-ynyl) 2,2-dimethyl clcyl-propanecarboxylate, (2,3,5,6-tetrafluoro phenyl)-methyl [1R-1α, 3α (E)]] 3-(2-trifluoromethyl)but-1-en-3-ynyl 2,2-dimethyl cyclopropanecarboxylate, and 2,3,5,6-tetrafluorophenyl)-methyl [1R-[1α, 3α (E)]] 3-(2-trifluoromethyl) pent-1-en-3-ynyl) 2,2-dimethyl cyclopropanecarboxylate.

11. An insecticidal composition comprising an insecticidally effective amount of a compound of claim 1 and an inert carrier.

12. A method of combatting insects comprising contacting insects with an insecticidally effective amount of a compound of claim 1.

* * * * *